United States Patent [19]
Chang et al.

[11] Patent Number: 5,961,766
[45] Date of Patent: Oct. 5, 1999

[54] METHOD FOR SELECTING A SUBSTRATE INTENDED FOR USE IN A CUTTING OPERATION

[75] Inventors: Eng-Pi Chang, Arcadia; Yao-Feng Wang, Diamond Bar, both of Calif.

[73] Assignee: Avery Dennison Corporation, Pasadena, Calif.

[21] Appl. No.: 09/062,206

[22] Filed: Apr. 17, 1998

[51] Int. Cl.[6] .......................... B32B 31/14; B32B 31/18; G01N 3/00; G01N 3/08
[52] U.S. Cl. .......................... 156/247; 156/248; 156/250; 156/268; 73/788; 73/827
[58] Field of Search .................. 73/150 A, 788, 73/827, 842, 856; 156/268, 247, 64

[56] References Cited

U.S. PATENT DOCUMENTS

| | | | |
|---|---|---|---|
| 3,580,065 | 5/1971 | Strittmater et al. | 73/150 A |
| 3,788,135 | 1/1974 | Hammond, Jr. | 73/150 A |
| 4,153,496 | 5/1979 | Swift | 156/384 |
| 4,246,058 | 1/1981 | Reed | 156/183 |
| 4,328,057 | 5/1982 | Gutow | 156/248 |
| 4,501,154 | 2/1985 | Mori | 73/827 |
| 4,612,805 | 9/1986 | Bruce et al. | 73/150 A |
| 4,893,503 | 1/1990 | Kimura et al. | 73/150 A |
| 4,899,581 | 2/1990 | Allen et al. | 73/150 A |
| 4,957,004 | 9/1990 | McKinlay et al. | 73/842 |
| 4,958,521 | 9/1990 | Morimoto et al. | 73/827 |
| 5,331,858 | 7/1994 | Theller | 73/827 |
| 5,404,751 | 4/1995 | Beran et al. | 73/150 A |
| 5,696,327 | 12/1997 | Huang et al. | 73/845 |
| 5,700,564 | 12/1997 | Freedman | 428/332 |

OTHER PUBLICATIONS http://www.stablemicrosystems.com/ pp. 1,4–8, 11,27–28 of enclosure, 1996.

Chuang et al., Adhesive Age, Sep. 1997, pp. 18–23, "Avery Adhesive Test Yields More Performance Data Than Traditional Probe".

*Primary Examiner*—Mark A. Osele
*Assistant Examiner*—Sue A. Purvis
*Attorney, Agent, or Firm*—Renner, Otto, Boisselle & Sklar, P.L.L.

[57] ABSTRACT

This invention relates to a method for selecting a substrate intended for use in a cutting operation. The method is particularly suitable for selecting facestock materials intended for use in making pressure-sensitive adhesive (PSA) constructions such as PSA labels. The method includes the following steps (A)–(D). Step (A) involves cutting the substrate during a first cutting step to form at least two shapes in the substrate. The shapes are positioned in spaced relationship to each other. A matrix is formed during this cutting step. The matrix is the waste substrate material around the shapes. Step (B) involves cutting the substrate with a second cutting step to form a test sample. The test sample is comprised of part of one shape, part of the next adjacent shape, and the matrix around the shape parts. Step (C) involves separating the matrix from the shape parts while measuring the force required to separate the matrix from the shape parts and measuring the displacement of the separating force. Step (D) involves determining the friction energy required to separate the matrix from the shape parts. The selection of the substrate is dependent on the friction energy.

32 Claims, 8 Drawing Sheets

METHOD FOR SELECTING A SUBSTRATE INTENDED FOR USE IN A CUTTING OPERATION

TECHNICAL FIELD

This invention relates to a method for selecting a substrate intended for use in a cutting operation. More particularly, this invention relates to a method for selecting a substrate that is to be subjected to a cutting operation, wherein the friction energy required to separate a waste matrix from cut shapes formed in the substrate is determined and the selection of the substrate is dependent on the friction energy measurement. In one embodiment, the method is suitable for selecting facestock materials intended for use in making pressure-sensitive adhesive (PSA) constructions such as PSA labels.

BACKGROUND OF THE INVENTION

It has long been known to manufacture and distribute PSA stock for labels by providing a layer of face or facestock material for the label or sign backed by a layer of a PSA which in turn is covered by a release liner or carrier. The liner or carrier protects the adhesive during shipment and storage and allows for efficient handling of an array of individual labels after the labels are die-cut and the matrix is stripped from the layer of facestock material and up to the point where the individual labels are dispensed in sequence on a labeling line. During the time from die-cutting to dispensing, the liner or carrier remains uncut and may be rolled and unrolled for storage, transit and deployment of the array of individual labels carried thereon.

Failure to reliably dispense is typically characterized by the label following the carrier around a peel plate without dispensing or "standing-off" from the carrier for application to the substrate. Such failure to dispense is believed to be associated with excessive release values between the label facestock material and the liner. Dispensibility also is dependent upon the stiffness of the facestock. Failure to dispense may also be characterized by the wrinkling of the label due to lack of label stiffness at the dispensing speed as it is transferred from the carrier to the substrate. Another particular need in many labeling applications is the ability to apply polymeric-film labels at high line speeds, since an increase in line speed has obvious cost saving advantages.

In many label applications, it is desirable that the facestock material be a film of polymeric material which can provide properties lacking in paper, such as clarity, durability, strength, water-resistance, abrasion-resistance, gloss and other properties. It is desirable to reduce the thickness or "down-gauge" the facestock material in order to attain savings in material costs. Such reduction in facestock thickness often has resulted in reduced stiffness and the inability to die-cut and dispense the labels in a reliable commercially acceptable manner using automatic machinery.

A problem with these thin polymeric facestocks is that it is difficult to predict their die-cutting characteristics. Good die-cutting requires that the die cuts through the facestock and adhesive, but stops short of the silicone-coated release liner. Incomplete or poor die-cutting results in the labels failing to separate from the waste matrix material during subsequent separating of the matrix. Overcutting (i.e., heavy die strike on the liner or deep cut into the liner) creates problems during high speed dispensing. These problems include labels going around the peel tip assembly with the liner, or liner breakage due to the weakness induced by the die cutting partially into the liner.

There are two generally accepted techniques for measuring die-cuttability. One of these techniques involves using a multilevel die with different blade cutting depths and combinations of different bearer-anvil compressive forces. The die-cuttability of the PSA construction is determined by noting the minimum blade cutting depth or minimum compressive force needed for a non-fuzzy, clean, die-cut edge. The other technique involves manually separating and visually observing a die-cut sample against the light. Good die-cuttability is indicated by an easy and clean removal of the label from the matrix. The edge of a separated label exhibiting good die-cut characteristics looks clean and does not show signs of a roughened edge, fuzziness and stretching, or tickers hanging on the die-cut edge. Both of these methods are costly, time consuming, nonquantitative and operator subjective.

The present invention eliminates these shortcomings by employing a quick, reliable and quantitative test for selecting facestock materials by providing an accurate prediction of the die-cutting characteristics of such facestock materials. The test used with the inventive method provides a single number or value for measuring die-cuttability, this number being referred to as the friction energy required to separate the waste matrix from die-cut shapes cut in the facestock material. This test can be conducted in a laboratory using laboratory-size, die-cutting apparatus and relatively small test samples. The inventive method is useful in selecting facestock materials for use in making PSA constructions as well as in selecting other substrates that are to be subjected to cutting operations. The method is particularly suitable for selecting relatively thin facestock materials that are difficult to die-cut.

The substrate selection method of the invention eliminates the need to manufacture large master rolls of material for testing of die cutting, instead requiring only hand-sheet samples. This represents a significant savings of time and money, e.g., by avoiding scrap during testing. The selection method provides a means for generating quantitative data on sheet material cutting characteristics in an efficient, economical manner.

SUMMARY OF THE INVENTION

This invention relates to a method for selecting a substrate intended for use in a cutting operation, said method comprising:

(A) cutting said substrate during a first cutting step to form at least two shapes in said substrate, the shapes being positioned in spaced relationship to each other, a matrix being formed during said first cutting step, said matrix comprising the waste substrate around the shapes;

(B) cutting the substrate with a second cutting step to form a test sample; said test sample comprising part of one shape, part of another shape adjacent to said one shape, and the matrix around said shape parts;

(C) separating said matrix from the shape parts of said test sample while measuring the force required to separate said matrix and measuring the displacement of the separating force;

(D) determining the friction energy required to separate the matrix from the shape parts for said substrate, the selection of said substrate being dependent on said friction energy measurement.

In one embodiment, the invention relates to a method for selecting a facestock for use in a pressure-sensitive adhesive construction, said pressure-sensitive adhesive construction comprising said facestock, a layer of a pressure-sensitive adhesive, and a liner, the pressure-sensitive adhesive layer being positioned between the facestock and the liner and being preferentially adherent to the facestock; said method comprising:

(A) cutting the pressure-sensitive adhesive construction with a first cutting step to form at least two shapes; the shapes being positioned in spaced relationship to each other; the cut from the first cutting step being deep enough to penetrate the facestock; the cut from the first cutting step resulting in the formation of a matrix which comprises the waste facestock around the shapes;

(B) cutting the pressure-sensitive adhesive construction with a second cutting step to form at least one test sample; the test sample comprising part of one shape, part of another shape adjacent to said one shape, the matrix around said shape parts, and the adhesive and liner underlying the shape parts and matrix of the test sample;

(C) separating the matrix from the shape parts of said test sample while measuring the force required to separate the matrix from the test sample and measuring the displacement of said force; and (D) determining the friction energy required to separate the matrix from the shape parts for said facestock, the selection of such pressure-sensitive construction, or a portion of said construction, being dependent on such friction energy measurement.

In the embodiment in which the tested substrate is a pressure-sensitive construction or facestock therefor, in addition to selecting the substrate depending on the friction energy measurements, other properties may be considered in the selection. For example, the stiffness and dispensibility of the construction, its strength, printability, and its clarity and other appearance properties, all may be important factors in the selection of a suitable facestock.

BRIEF DESCRIPTION OF THE DRAWINGS

In the annexed figures, like references indicate like parts or features.

DESCRIPTION OF THE PREFERRED EMBODIMENTS

The substrate that can be selected pursuant to the inventive method can be any sheet or film substrate intended for use in a cutting operation. These substrates include metal foils, polymer films, paper, and combinations thereof. The substrates can be textiles including woven and non-woven fabrics made of natural or synthetic fibers. The substrates can be single-layered sheets or films or they can be multi-layered constructions. These include polymeric films and multi-layered polymeric films. The multi-layered constructions and polymeric films have two or more layers, and in one embodiment about two to about seven layers, and in one embodiment about three to about five layers. The layers of such multi-layered constructions and polymeric films can have the same composition and/or size or they can be different. The substrate can be any of the above sheet or film materials, and in addition the substrate can include a facestock or backing layer of such a material, in combination with other layers such as a pressure-sensitive adhesive, a top coating, etc. The substrate can have any thickness that is suitable for sheet or film substrates intended for use in cutting operations, with thicknesses in the range of about 0.3 to about 20 mils, and in one embodiment about 0.3 to about 10 mils, and in one embodiment about 0.5 to about 5 mils, and in one embodiment about 0.5 to about 4 mils, and in one embodiment about 0.5 to about 3.8 mils, and in one embodiment about 0.5 to about 3.5 mils, and in one embodiment about 0.5 to about 3 mils, and in one embodiment about 1 to about 2.5 mils, being useful.

The metal foils include foils of such metals as copper, gold, silver, tin, chromium, zinc, nickel, platinum, palladium, iron, aluminum, steel, lead, brass, bronze, and alloys of the foregoing metals. Examples of such alloys include copper/zinc, copper/silver, copper/tin/zinc, copper/phosphorus, chromium/molybdenum, nickel/chromium, nickel/phosphorous, and the like. The metal foils can be joined or adhered to a polymeric sheet or film to form a multi-layered laminate or construction. Examples of the polymer sheets and films that can be joined to these metal foils include polyimide and polyester sheets and films.

The polymer films include polyolefins (linear or branched), polyamides, polystyrenes, nylon, polyesters, polyester copolymers, polyurethanes, polysulfones, polyvinylidine chloride, styrene-maleic anhydride copolymers, styrene-acrylonitrile copolymers, ionomers based on sodium or zinc salts of ethylene methacrylic acid, polymethyl methacrylates, cellulosics, fluoroplastics, acrylic polymers and copolymers, polycarbonates, polyacrylonitriles, and ethylene-vinyl acetate copolymers. Included in this group are the acrylates such as ethylene methacrylic acid, ethylene methyl acrylate, ethylene acrylic acid and ethylene ethyl acrylate. Also, included in this group are polymers and copolymers of olefin monomers having, for example, 2 to about 12 carbon atoms, and in one embodiment 2 to about 8 carbon atoms. These include the polymers of α-olefins having from 2 to about 4 carbon atoms per molecule. These include polyethylene, polypropylene, poly-1-butene, etc. An example of a copolymer within the above definition is a copolymer of ethylene with 1-butene having from about 1 to about 10 weight percent of the 1-butene comonomer incorporated into the copolymer molecule. The polyethylenes that are useful have various densities including low, medium and high density ranges. The low density range is from about 0.910 to about 0.925 g/cm$^3$; the medium density range is from about 0.925 to about 0.940 g/cm$^3$; and the high density range is from about 0.940 to about 0.965 g/cm$^3$. Films prepared from blends of copolymers or blends of copolymers with homopolymers also are useful. The films may be extruded as monolayered films or multi-layered films.

The paper substrates include paper, clay coated paper, glassine, paperboard from straw, bark, wood, cotton, flax, cornstalks, sugarcane, bagasse, bamboo, hemp, and similar cellulose materials prepared by such processes as the soda, sulfite or sulfate (Kraft) processes, the neutral sulfide cooking process, alkali-chlorine processes, nitric acid processes, semi-chemical processes, etc. Although paper of any basis weight can be employed, paper having basis weights in the range of from about 20 to about 150 pounds per ream (lb/ream) are useful, and papers having weights in the range of from about 30 to about 60 lb/ream can be used.

The substrate can be a polymer-coated paper which is basically comprised of a sheet of paper that is coated on either one or both sides with a polymer coating. The polymer coating, which can be comprised of a high, medium, or low density polyethylene, polypropylene, polyester, and other similar polymer films, is coated onto the substrate surface to add strength and/or dimensional stability. The weight of these types of coated paper substrates can vary over a wide range with weights in the range of about 30 to about 100 lb/ream being useful. In total, the final coated paper substrate may be comprised of between about 10% and about 40% by weight polymer. For two-sided coatings, the quantity of polymer is approximately evenly divided between the top and bottom surface of the paper.

In one embodiment, the substrate is an adhesive construction wherein an adhesive layer is applied to one side of the substrate, the substrate being a facestock. Typically, the adhesive layer has a thickness in the range of from about 0.1 to about 2 mils. The adhesives that can be used include pressure-sensitive adhesives, heat-activated adhesives, hot-melt adhesives, and the like. Pressure-sensitive adhesives are especially useful. The adhesives include acrylic based adhesives as well as other elastomers such as natural rubber or synthetic rubbers containing polymers or copolymers of styrene, butadiene, acrylonitrile, isoprene or isobutylene.

The substrate may comprise a pressure-sensitive adhesive construction including a facestock coated with a PSA, or alternatively may include only the facestock. A typical PSA construction comprises the facestock, a liner or backing material, and a layer of a pressure-sensitive adhesive. The pressure-sensitive adhesive is positioned between the facestock and the liner. The surface of the liner in contact with the adhesive is typically coated with a release agent. Because of this release coating, the strength of the adhesive bond to the facestock is greater than to the liner. That is, the pressure-sensitive adhesive is preferentially adherent to the facestock. Thus, when the liner is removed from the facestock, the pressure-sensitive adhesive remains adhered to the back of the facestock. The facestock can be comprised of one or more layers of any of the above-described substrate materials or combination of materials. Similarly, the liner may also be comprised of one or more layers of any of the above-discussed substrate materials or combination of materials.

The cut made during the cutting step (A) of the inventive method can be a continuous cut, a perforated cut, a microperforated cut, a scoring cut, a slitting cut, or a die-cut. The die-cut can be a cylinder-profile die cut or a flat-die cut. The cut may be made using mechanical cutting techniques, or alternatively via laser cutting.

Figures 1, 2, 3, 4A, 4B, 5:
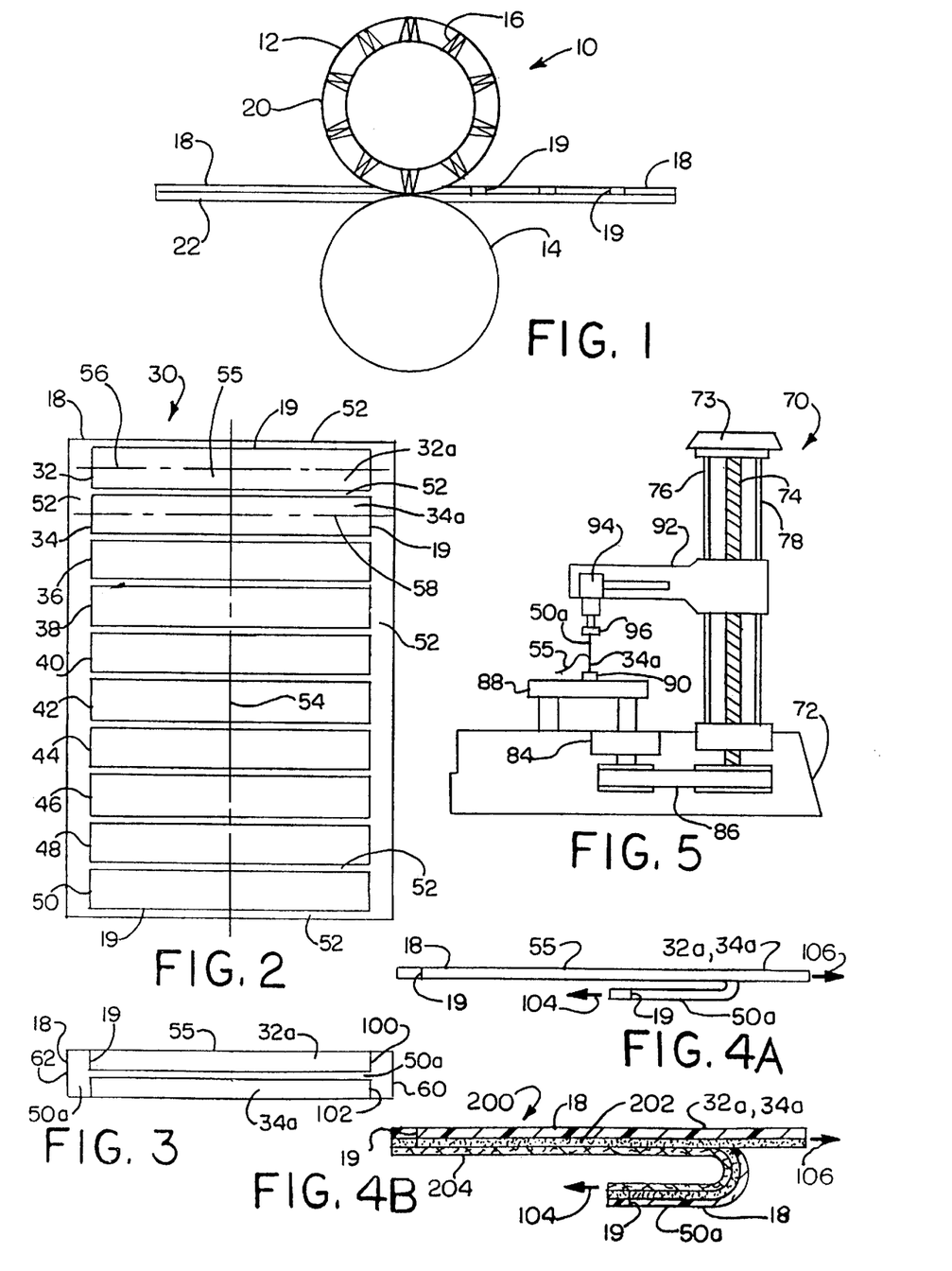
FIG. 1 is a schematic illustration of a die-cutting step that is useful as the first cutting step (A) of the inventive method.
FIG. 2 is a top plan view of a test sheet of a cut substrate formed during step (A) of the inventive method.
FIG. 3 is a top plan view of a test sample that is formed during step (B) of the inventive method.
FIG. 4A is a side elevation of the test sample illustrated in FIG. 3 with part of the matrix being separated from shape parts of the test sample, the test sample being a monolayer sheet or film.
FIG. 4B is a side elevation of an alternative embodiment of the test sample illustrated in FIG. 3 with part of the matrix being separated from the shape parts of the test sample, the test sample being a PSA construction.
FIG. 5 is a schematic illustration of a tensile testing device that is useful with the inventive method.
Figure 6A:
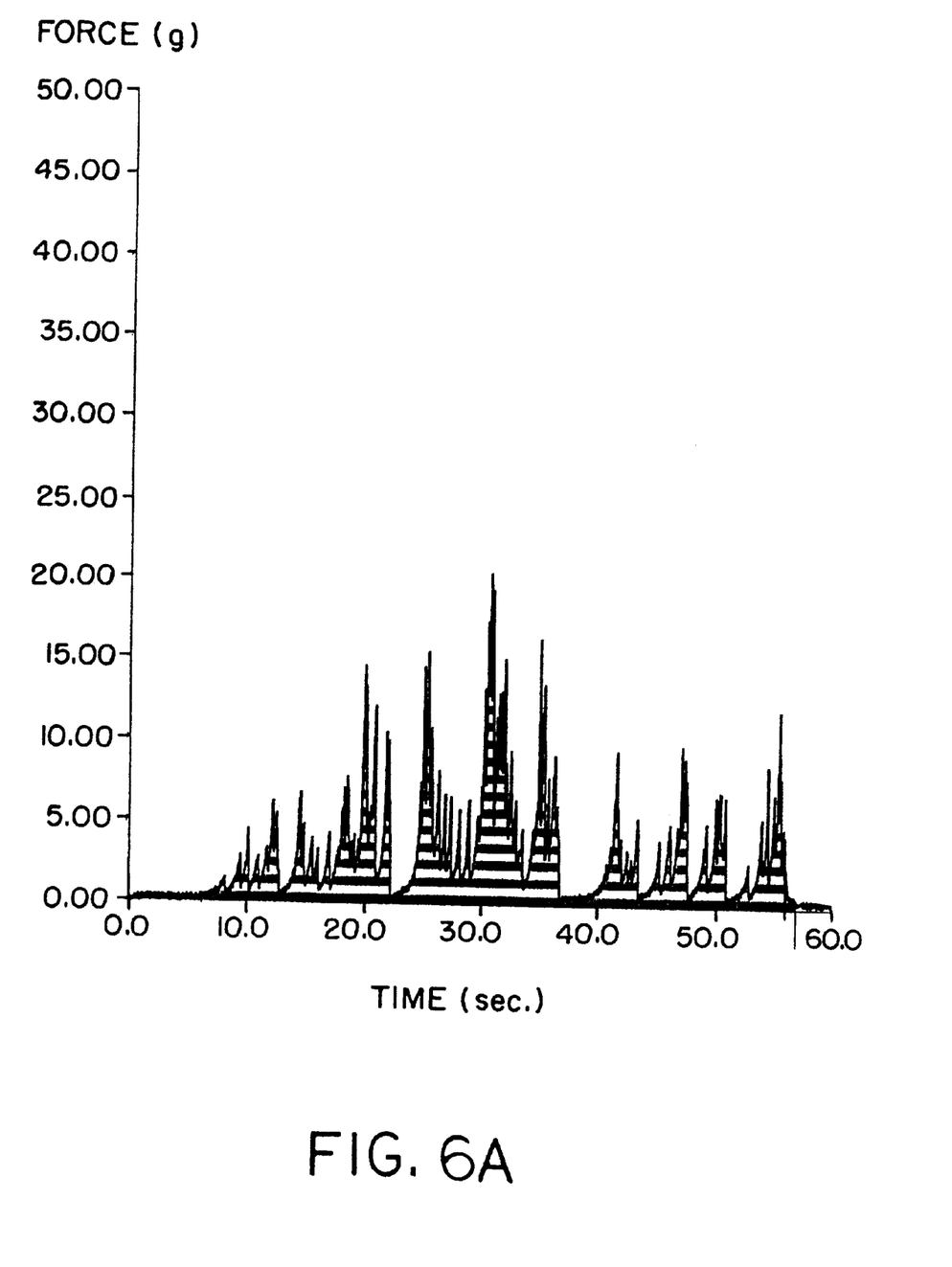
FIGS. 6A to 6G are force versus displacement plots made for Samples A–G of the Example.
Figure 6B:
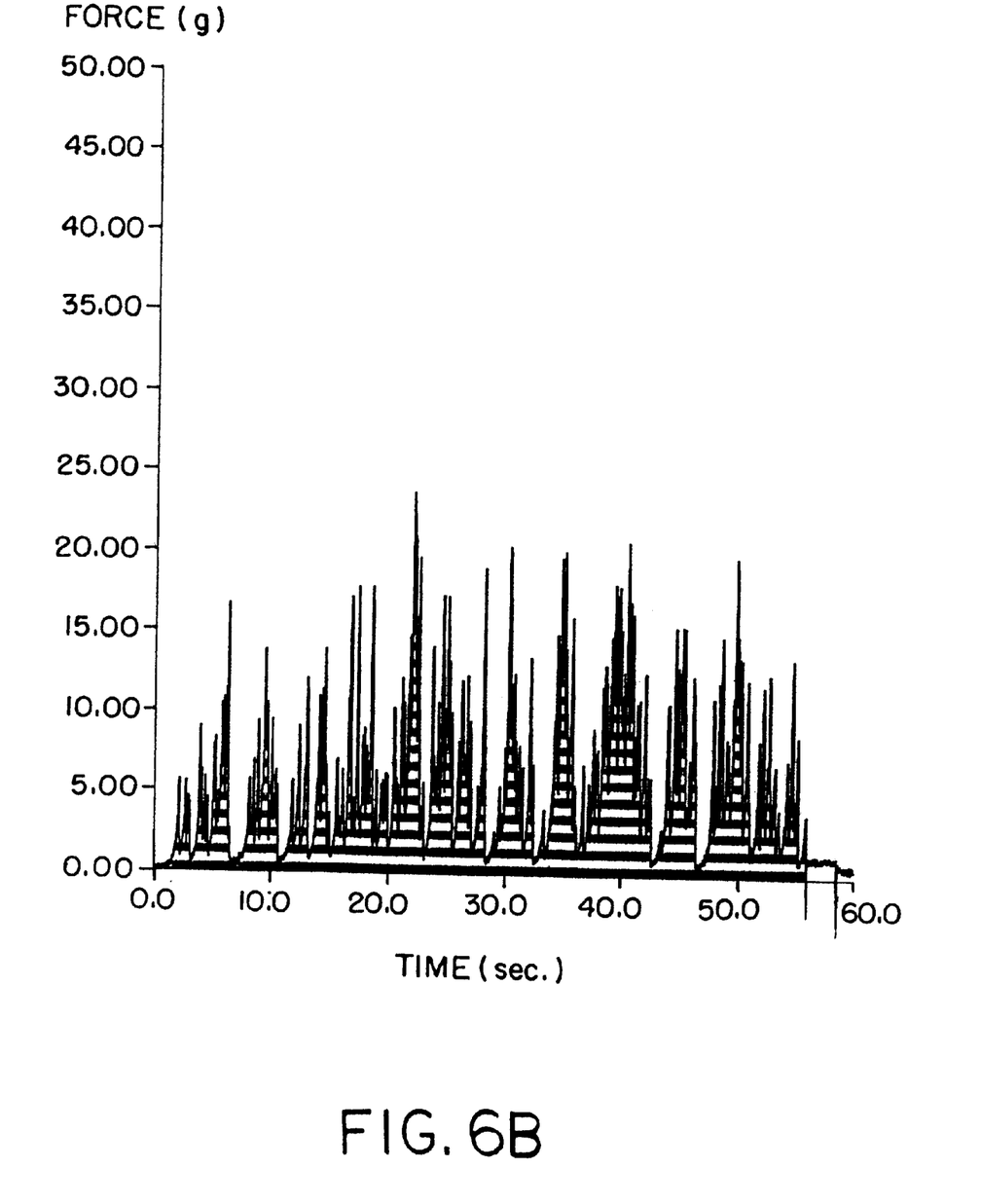
Figure 6C:
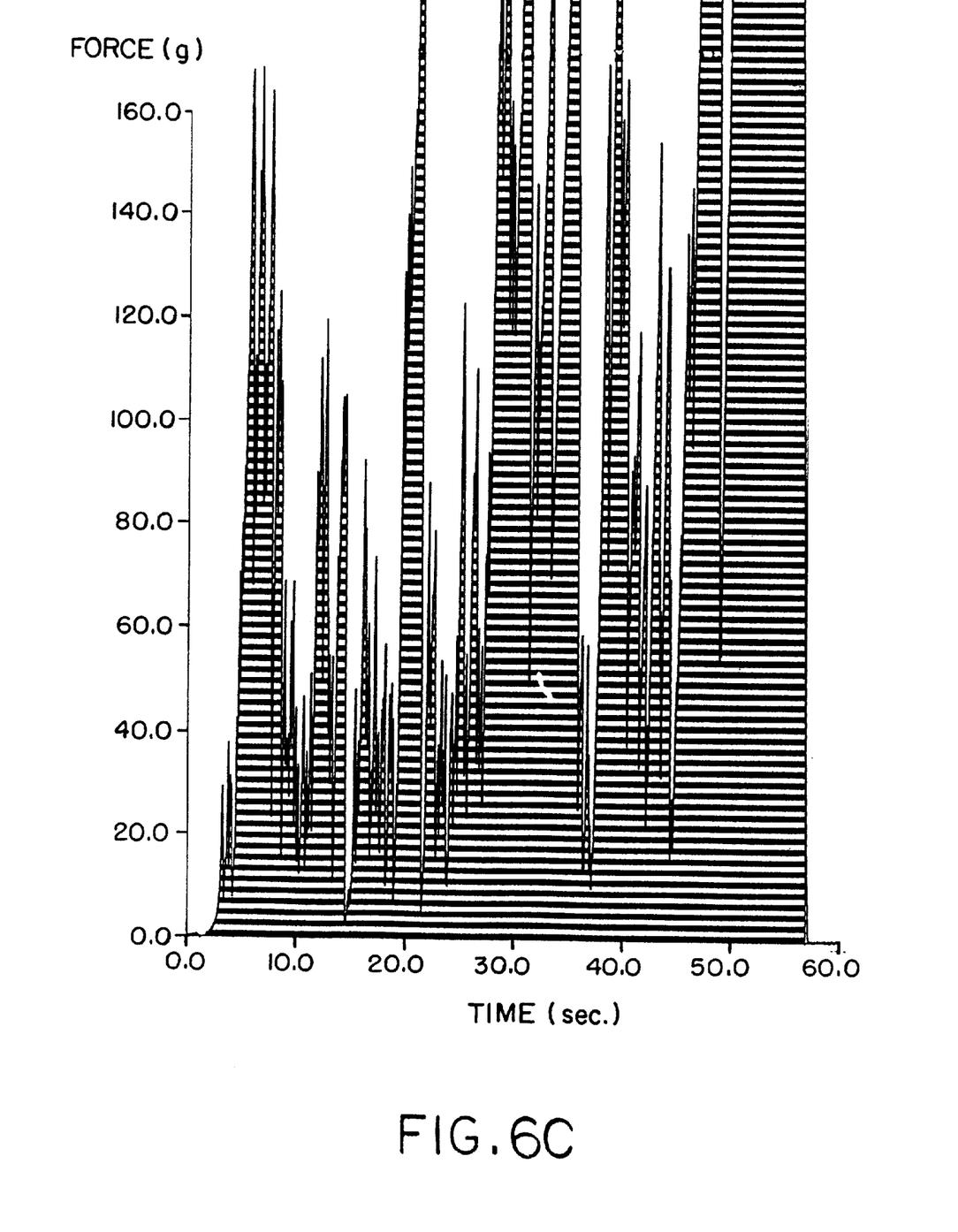
Figure 6D:
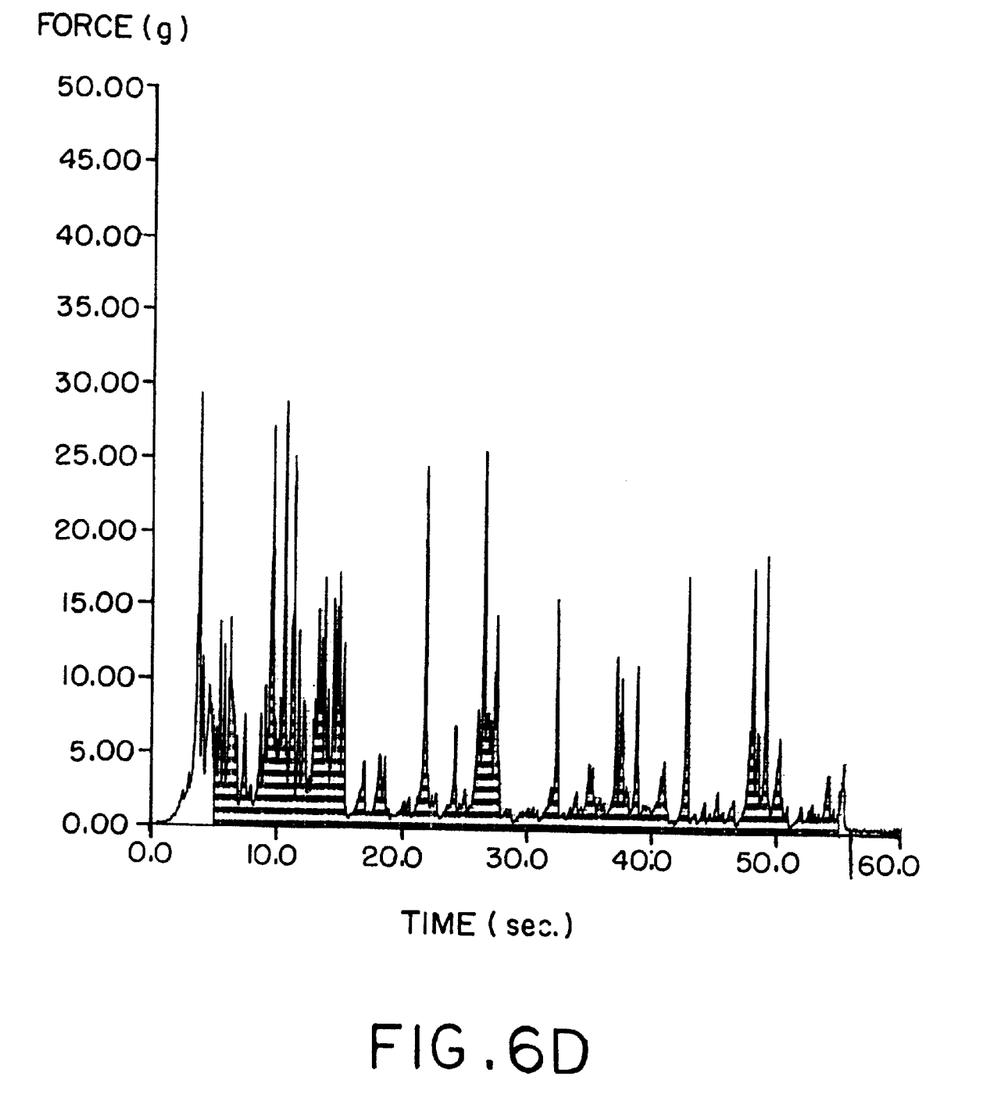
Figure 6E:
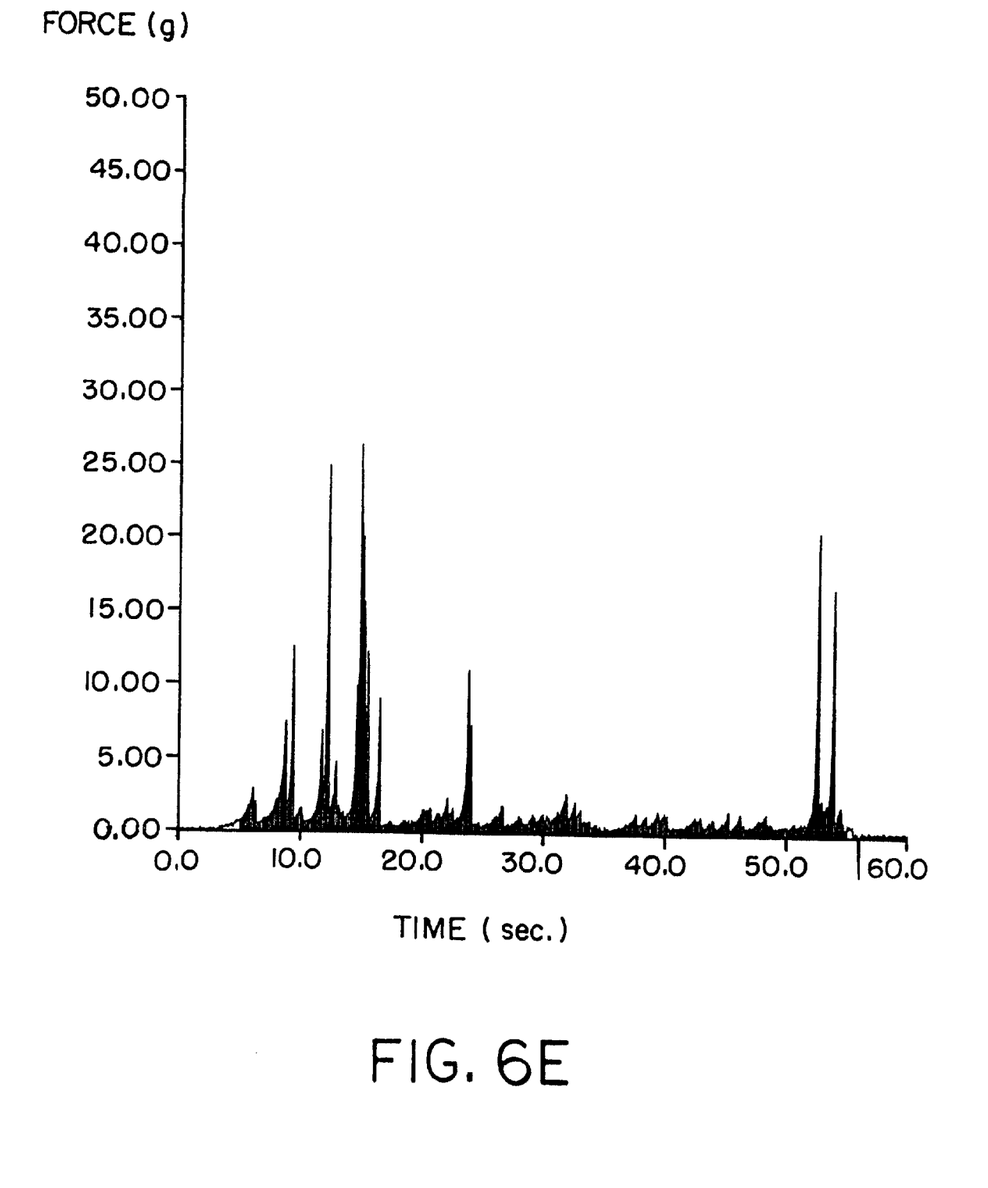
Figure 6F:
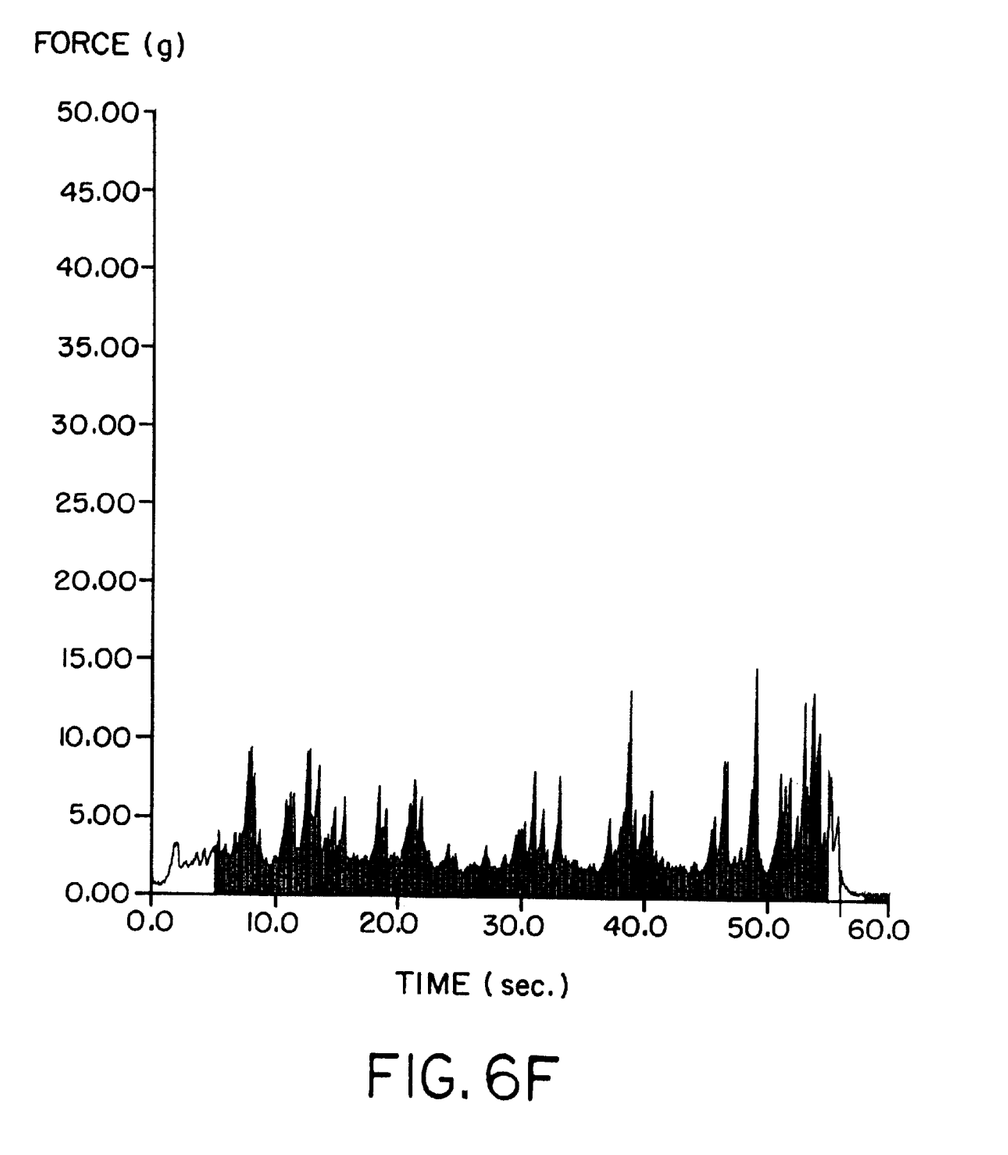
Figure 6G:
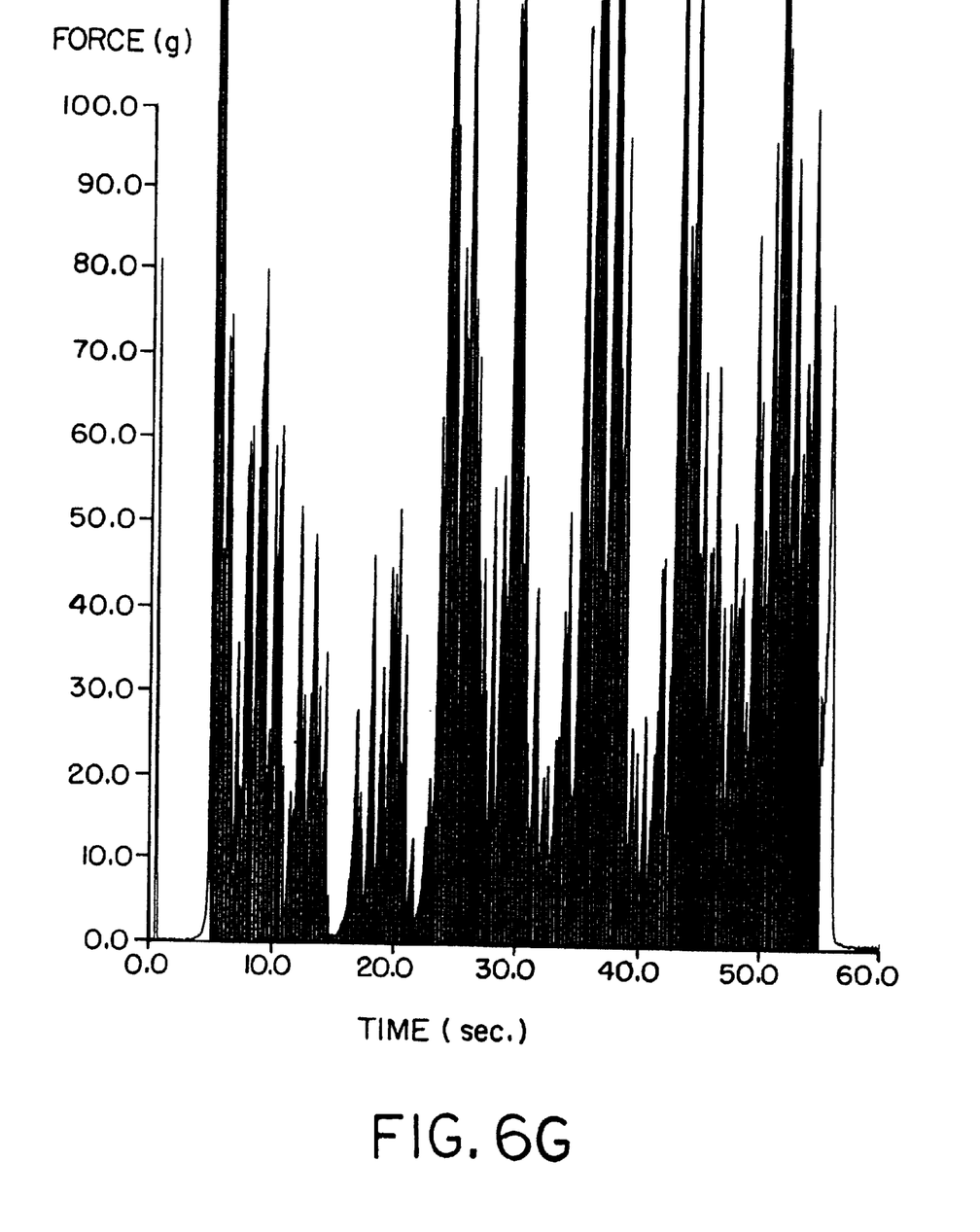

In one embodiment of the invention, the cutting step (A) is performed using a die-cutter with a cylinder profile of the type illustrated in FIG. 1. The die-cutter 10 illustrated in FIG. 1 has a die-cutting roll 12 and an anvil roll 14. The die-cutting roll 12 has an array of sharpened edges 16 formed in its surface to provide for the desired die-cut pattern in the substrate 18. The die-cutting roll 12 also has a bearer 20 on each of its ends to provide a desired separation between the sharpened edges 16 and the surface of the anvil roll 14 during die-cutting.

In operation, the substrate 18 is advanced through the die-cutter 10 and the desired cuts 19 are cut in the substrate 18. In one embodiment, the substrate is a mono-layered or multi-layered film or construction and it is desired that the cut penetrates the entire thickness of the substrate. In this embodiment, it is preferable to place a layer of sheet or film 22 (e.g., a paper or film liner) under the substrate and advance the substrate 18 and the underlying layer of sheet or film 22 through the die-cutter together with the underlying layer of sheet or film 22 in contact with the anvil roll 14. In one embodiment, the substrate is part of a multi-layered construction such as a PSA construction and it is desired that the pattern be cut in the substrate, but not the remaining underlying layer or layers of the construction. In this embodiment, the multi-layered construction can be advanced through the die-cutter by itself. For example, when a PSA construction is cut pursuant to step (A) of the inventive method, the facestock and underlying adhesive layer may be cut, but not the liner. The cuts 19 can be continuous cuts, perforated cuts, microperforated cuts, etc.

The cutting step (A) of the inventive method provides a cut test sheet such as the die-cut test sheet 30 illustrated in FIG. 2. Die-cut test sheet 30 is comprised of die-cut shapes 32, 34, 36, 38, 40, 42, 44, 46, 48 and 50, and matrix 52 which is the waste substrate material around the die-cut shapes. In the illustrated embodiment, the die-cut shapes are rectangular in shape and arranged side-by-side in an array, one across and ten deep. The die-cut shapes are of equal size and aligned along a common centerline 54. The long dimension of each of the die-cut shapes is parallel to the long dimension of the next adjacent shape. Although the illustrated shapes are rectangular, it is to be understood that any shape that can be cut from a sheet or film substrate can be used including triangles, squares, circles, polygons, irregular shapes, and the like.

A test sample 55 is formed by cutting the test sheet 30 along parallel lines 56 and 58. Line 56 is the centerline of shape 32, and line 58 is the centerline of shape 34. The test sample 55, which is best illustrated in FIG. 3, is comprised of part 32a (i.e., one-half) of shape 32, part 34a (i.e., one-half) of shape 34, and the part 52a of matrix 52 between the shape parts 32a and 34a and on the edges 60 and 62 of test sample 55. Additional test samples similar to test sample 55 can be cut from test sheet 30.

The friction energy required to separate the matrix part 52a from the shape parts 32a and 34a of test sample 55 can be determined by separating the matrix part 52a from the shape parts 32a and 34a using a tensile testing device while measuring the force required to separate the matrix part 52a from the shape parts 32a and 34a and measuring the displacement of the force along the length of the test sample 55 during this separating. The tensile testing device can be any apparatus suitable for testing the tensile strength of sheet or film substrates that is equipped with appropriate hardware and software for measuring the force required to effect the separating and measuring the displacement of the force along the length of the test sample during such separating.

In one embodiment, a tensile testing device 70 is schematically illustrated in FIG. 5. This device has a base 72, an upper frame 73, a rotatable screw 74 projecting vertically from the base 72 to the upper frame 73, and vertical guides 76 and 78 projecting vertically from base 72 to upper frame 73. A step motor 84 and a drive belt 86 are mounted on the base and are provided for rotating screw 74. A platform 88 is mounted on base 72 and an lower L-shaped bracket 90 is mounted on platform 88. A cantilevered arm 92 is supported by screw 74 and vertical guides 76 and 78, and is adapted for upward or downward movement with the rotation of screw 74. Transducer 94 is mounted on cantilevered arm 92. Upper L-shaped bracket 96 depends from transducer 94.

The test sample 55 is mounted on the testing device 70 while the cantilevered arm 92 is in a lowered position. End 60 of matrix part 52a is attached to bracket 96 and ends 100 and 102 of shape parts 32a and 34a, respectively, are attached to bracket 90. Step motor 84 is activated. This rotates belt 86 which turns screw 74. The turning of screw 74 causes cantilevered arm 92 to move upwardly. The upward movement of cantilevered arm 92 places a tensile force on test sample 55. This tensile force causes matrix part 52a to separate from shape parts 32a and 34a as the cantilevered arm 92 moves upwardly.

The separating force applied to the matrix part 52a is at an angle of about 180° relative to the force holding shape parts 32a and 34a in bracket 90 during the separating. This is illustrated in FIG. 4 wherein the force indicated by directional arrow 104 applied to matrix part 52a during the separating is at an angle of about 180° relative to the force applied to shape parts 32a and 34a as indicated by directional arrow 106 during such separating. In an alternate embodiment, the test sample 55 can be rotated 90° when placed in the testing device 70 and the force applied during the separating can be at an angle of about 90°.

As indicated above, the substrate can be the facestock of a PSA construction. This is illustrated in FIG. 4B. The test sample 200 illustrated in FIG. 4B is similar to the test sample 55 illustrated in FIGS. 3 and 4A except that test sample 200 has a layer of a pressure-sensitive adhesive adhered to its underside and a liner adhered to the pressure-sensitive adhesive. The PSA construction test sample 200 has a facestock 18, a PSA layer 202 underlying and adhered to the facestock 18, and release coated liner 204 underlying and adhered to the pressure-sensitive adhesive 202. The pressure-sensitive adhesive 202 is preferentially adherent to the facestock 18. The cuts 19 formed during the cutting step (A) of the inventive method are deep enough to penetrate the facestock 18 and the adhesive 202, but not the liner 204. During the separating step (C) of the inventive method, the matrix part 52a is separated from the shape parts 32a and 34a. The part of the adhesive layer 202 underlying the shape parts 32a and 34a remains adhered to shape parts 32a and 34a. The part of the adhesive layer 202 underlying the matrix part 52a remains adhered to matrix part 52a. The liner 204 remains adhered to shape parts 32a and 34a. The force indicated by directional arrow 104 applied to matrix part 52a during the separating is at an angle of about 180° relative to the force applied to shape parts 32a and 34a indicated by directional arrow 106 during such separating. In an alternate embodiment, the test sample 200 can be rotated 90° when placed in the testing device 70 and the force applied during the separating can be at an angle of about 90°.

The force applied to the test sample 55 or 200 during the separating and the displacement of the force along the test sample are measured, and the friction energy required to separate the matrix from the shape parts is determined from these measurements. This can be done by integrating the force times the differential displacement measurements, the result of this integration being a measure of the friction energy. Commercially available hardware and software is available for determining this measurement. Alternatively, the force and the displacement of the force along the length of the sample is plotted using commercially available hardware and software, and the area under the plot is determined, this area being a measure of the friction energy. The area under the plot can be determined using known integration techniques and commercially available hardware and software. Alternatively, the area under the plot can be measured by counting the number of square centimeters under the plot or by cutting out the area under the plot and weighing it. The area under the plot is typically measured in terms of force (grams) versus time (seconds), and can be converted to force (grams) versus displacement (centimeters) by multiplying the area under the force-time plot by the speed of the separating movement (i.e., the speed of the upward movement of cantilevered arm 92). This results in the obtaining of a number or value, referred to herein as friction energy number or value, required to separate the matrix part 52a from the shape parts 32a and 34a.

The substrate to be selected for the desired cutting operation is selected on the basis of the friction energy number or value determined by the foregoing method. This is done by testing several candidate substrates and selecting the substrate with the desired friction energy number or value, which in most instances will be the substrate with the lowest friction energy number or value.

When testing a multi-layer substrate for friction energy values, the method of the invention may be used to select the entire substrate, or a layer from the substrate, or certain layers from the substrate. For example, where the substrate comprises a pressure-sensitive adhesive construction comprising a facestock coated with a pressure-sensitive adhesive, the method may be used to select the facestock, the pressure-sensitive adhesive, or the entire construction.

It is to be understood that references to "facestock" herein are also intended to include other types of PSA-coated backings which are not normally considered facestocks.

EXAMPLE

The inventive method is illustrated by the testing of the following Samples A–G. Samples A–E are polymeric films. Samples F and G are PSA constructions.

Sample A is a filmic sheet of a uniaxially oriented multi-layered polypropylene/ethylene vinyl acetate copolymer blend having a thickness of 3.5 mils commercially available from Avery Dennison under the name Primax® 350.

Sample B is a filmic sheet of a uniaxially oriented multi-layered polypropylene/ethylene vinyl acetate copolymer blend having a thickness of 2.5 mils commercially available from Avery Dennison under the name Fasclear® 250.

Sample C is a filmic sheet of a uniaxially oriented single-layered polypropylene having a thickness of 3.0 mils commercially available from Avery Dennison under the name Mirage® 300.

Sample D is a multi-layered film. The film has the following construction, reading from the top surface of the film to the opposite bottom surface:

|  | % of Film Thickness |
|---|---|
| Rexene 2030 | 10 |
| EM 803-115 | 5 |
| WRD5-1057 | 70 |

-continued

| | % of Film Thickness |
|---|---|
| EM 803-115 | 5 |
| Rexene 2030 | 10 |

Rexene 2030 is a product of Rexene identified as a polyethylene having a density of 0.919 g/cm$^3$. EM 803-115 is a product of Equistar identified as copolymer of low-density polyethylene and methylacrylate. WRD 5-1057 is a product of Union Carbide identified as polypropylene. The multilayered film has a thickness of 2.25 mils.

Sample E is the same as Sample D except that the middle or core layer of the film has a composition of 99% by weight WRD5-1057, and 1% by weight 8C41-10 which is a product supplied by Millad identified as a sorbitol-type nucleating agent. Sample F is a PSA construction having a layer of Fasclear® 350 as the facestock. Fasclear® 350 is the same as Fasclear® 250 except that the film thickness is 3.5 mils. The pressure-sensitive adhesive is an acrylic adhesive. The thickness of the pressure-sensitive adhesive layer is 0.8 mils. The liner is a 40 lb/ream glassine release liner.

Sample G is a PSA construction having a monolayer of a polypropylene cast film with a thickness of 2.5 mils as the facestock. The pressure-sensitive adhesive is an acrylic adhesive. The thickness of the pressure-sensitive adhesive layer is 0.8 mils. The liner is a 40 lb/ream glassine release liner.

A test sheet of each sample having the dimensions of 7×10"(17.8×25.4 cm) is advanced through a die-cutter where ten shapes are cut in the film of Samples A–E and the facestock of Samples F–G. The die-cutter is schematically illustrated in FIG. 1 and the die-cut test sheet is schematically illustrated in FIG. 2. During the die-cutting step, Samples A–E are placed on a 40 lb/ream liner and advanced through the die-cutter. Samples F–G are advanced through the die-cutter by themselves. The die-cutter has a cylindrical profile. The die-cutting roll has a diameter of 3 inches (76.2 mm), with one cavity across and ten cavities around. Each of the cavities are 6 inches (152.4 mm) long (or across), $^{15}/_{16}$ inch (22.25 mm) wide (or deep) and have rounded corners with diameters of $^{3}/_{32}$ inch (2.38 mm). The separation between adjacent cavities is ⅛ inch (3.175 mm). The anvil roll has a diameter of 5 inches (127 mm). The gap between the anvil and the tip of the die is 2.2 mils (0.0559 mm). The die pressure is 300 psi (218180 kg/m$^2$), and the speed of the die is 15 m/min.

The die-cut in each test sheet is deep enough to penetrate the film of Samples A–E, and the facestock and pressure-sensitive adhesive but not the release liner of Samples F–G. The shapes that are formed are rectangular in shape and arranged side-by-side on the test sheet, one shape across and ten deep as illustrated in FIG. 2. The long dimension of each shape is parallel to the long dimension of the next adjacent shape. The shapes have the dimensions of ⅞×6"(22.25 mm×152.4 mm) and are equidistant from each other. The gap between each shape is ⅛ inch (3.175 mm). A matrix, which consists of the portion of the waste film or facestock around the shapes, is also formed during the die-cutting.

A test sample is formed by cutting the die-cut test sheet along the center line of the long dimension of one shape and then along the center line of the long dimension of the next adjacent shape. The cuts are parallel to each other. Each test sample consists of one-half of one shape, one-half of the next adjacent shape, and the matrix around the shape parts. The test samples for Samples F–G also include the adhesive and release liner underlying the shape parts and matrix. The test samples for Samples A–E are schematically illustrated in FIGS. 3 and 4A. The test samples for Samples F–G are schematically illustrated in FIGS. 3 and 4B.

The friction energy required to separate the matrix from the shape parts of each test sample is measured using a modified TA-XT2 Texture Analyzer provided by Stable Micro Systems, Unit 105, Blackdown Rural Industries, Haste Hill, Haslemere, Surrey GU 27 3AY, England. The TA-XT2 Texture Analyzer is a tensile testing device equipped with hardware and software for measuring the force required to separate the matrix from the shape parts and measuring the displacement of the separating force. This equipment provides a plot of the separating force versus time of separation and calculates the area under this plot. The device is modified as follows: the fixture on the top crosshead is removed and substituted by an upper L-shaped bracket; one arm of the upper L-shaped bracket is attached to the upper frame; the platform mounted on the base is removed and substituted by a lower L-shaped bracket. Each test sample is tested by attaching an edge of the matrix of the test sample to the upper L-shaped bracket, and attaching the edge of each label portion adjacent to the attached matrix edge to the lower L-shaped bracket. The texture analyzer is activated and the matrix is separated from the shape parts at a constant rate of 5 mm/s.

The force used to separate the matrix and the displacement of this force along the length of the test sample during separating is plotted using software provided with the TA-XT2 Texture Analyzer. The area under the plot is also determined using software provided with the TA-XT2 Texture Analyzer. The area under the plot has the units of gram-seconds. The result is multiplied by the separating speed (5 mm/s) and after making appropriate corrections for units (i.e., mm to cm), the friction energy results are provided in terms of gram-centimeters. Higher friction energy numbers are associated with poorly cut facestocks or adhesive flowback. The test results for Samples A–G are summarized below. For each of Samples A–G, 20 test samples are tested and the averages for these test samples are given below. Samples of each test sample are also manually separated and visually observed; these are ranked according to the quality of the die-cut pursuant to prior art techniques. The ranking of each sample is indicated below. A plot of force versus time made for one of the test samples for each of Samples A–G is shown in FIGS. 6A–6G, respectively. In this regard, FIG. 6A corresponds to Sample A, FIG. 6B corresponds to Sample B, etc.

TABLE I

| Sample | Friction Energy (g-cm) | Rank |
|---|---|---|
| A | 83 | 2 |
| B | 241 | 4 |
| C | 2281 | 5 |
| D | 164 | 3 |
| E | 78 | 1 |

TABLE II

| Sample | Friction Energy (g-cm) | Rank |
|---|---|---|
| F | 88 | 1 |
| G | 1118 | 2 |

For the die-cutting tests performed under the foregoing conditions, it is believed that test samples exhibiting friction energy numbers or values of 150 g-cm or less would be suitable for use in making die-cut PSA labels. Thus, the foregoing test results indicate that the films tested as Samples A and E and the facestock tested with Sample F would be suitable facestock materials for making PSA labels. The foregoing results also indicate that the friction energy test results are consistent with prior art subjective observation techniques.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method for selecting a substrate intended for use in a cutting operation, said method comprising:

(A) selecting a candidate substrate;

(B) cutting said candidate substrate during a first cutting step to form at least two shapes in said candidate substrate, the shapes being positioned in spaced relationship to each other, a matrix being formed during said first cutting step, said matrix comprising the waste candidate substrate around the shapes;

(C) cutting the candidate substrate with a second cutting step to form a test sample; said test sample comprising part of one shape, part of another shape adjacent to said one shape, and the matrix around said parts of said shapes;

(D) separating said matrix from said test sample while measuring the force required to separate said matrix and measuring the displacement of the separating force;

(E) determining the friction energy required to separate the matrix from the shape parts for said candidate substrate, and selecting the candidate substrate as said substrate if the friction energy determined for said substrate is acceptable.

2. The method of claim 1 wherein said substrate comprises a single-layered construction.

3. The method of claim 1 wherein said substrate comprises a multi-layered construction.

4. The method of claim 1 wherein said substrate comprises a foil, paper, polymer film, textile, or a combination thereof.

5. The method of claim 1 wherein the substrate is a pressure-sensitive adhesive construction.

6. The method of claim 1 wherein the substrate comprises a facestock and a pressure-sensitive adhesive, and wherein the selection of said substrate comprises the selection of the facestock of said substrate.

7. The method of claim 1 wherein said substrate is comprised of a polymeric film.

8. The method of claim 1 wherein said substrate is comprised of a multi-layered polymeric film.

9. The method of claim 1 wherein the cut formed during said cutting step (A) is a continuous cut.

10. The method of claim 1 wherein the cut formed during said cutting step (A) is a perforated cut.

11. The method of claim 1 wherein the cut formed during said cutting step (A) is a microperforated cut.

12. The method of claim 1 wherein the cut formed during said cutting step (A) is a scoring cut.

13. The method of claim 1 wherein the cut formed during said cutting step (A) is a slitting cut.

14. The method of claim 1 wherein said cutting step (A) is a laser cut.

15. The method of claim 1 wherein the cut formed during step (A) is a die-cut.

16. The method of claim 1 wherein the cut formed during step (A) is a cylinder-profile die cut.

17. The method of claim 1 wherein the cut formed during said cutting step (A) is a flat-die cut.

18. The method of claim 1 wherein more than two shapes are cut during step (A).

19. The method of claim 1 wherein the shapes that are cut during step (A) are of equal size and aligned along a common centerline.

20. The method of claim 1 wherein the shapes that are cut during step (A) are of equal size and rectangular in shape, the long dimension of each shape being parallel to the long dimension of the next adjacent shape.

21. The method of claim 1 wherein during step (C) the force used to separate said matrix from said test sample is at an angle of about 180° from said test sample.

22. The method of claim 1 wherein during step (C) the force used to separate said matrix from said test sample is at an angle of about 90° from said test sample.

23. The method of claim 1 wherein said separating step (C) is conducted using a tensile testing device equipped to measure the force required to effect said separating and the displacement of said force during said separating.

24. The method of claim 1 wherein said separating step (C) is conducted using a tensile testing device.

25. The method of claim 1 wherein said shapes are labels.

26. The method of claim 1 wherein said shapes are pressure-sensitive labels.

27. A method for selecting a facestock for use in a pressure-sensitive adhesive construction, said pressure-sensitive adhesive construction comprising said facestock, a layer of a pressure-sensitive adhesive, and a liner, the pressure-sensitive adhesive layer being positioned between the facestock and the liner and being preferentially adherent to the facestock; said method comprising:

(A) cutting the pressure-sensitive adhesive construction with a first cutting step to form at least two shapes; the shapes being positioned in spaced relationship to each other; the cut from this first cutting step being deep enough to penetrate the facestock; the cut from this first cutting step resulting in the formation of a matrix which comprises the waste facestock around the shapes;

(B) cutting the pressure-sensitive adhesive construction with a second cutting step to form at least one test sample; the test sample comprising part of one shape, part of another shape adjacent to said one shape, the matrix around said shape parts, and the adhesive and liner underlying the shape parts and matrix of the test sample;

(C) separating the matrix from the shape parts while measuring the force required to separate the matrix from the shape parts and measuring the displacement of said force; and (D) determining the friction energy required to separate the matrix from the shape parts for said facestock, the selection of such pressure-sensitive construction, or a portion of said construction, being dependent on such friction energy measurement.

28. A method for selecting the facestock of a pressure-sensitive adhesive construction, said pressure-sensitive adhesive construction comprising said facestock, a layer of a pressure-sensitive adhesive, and a liner, the pressure-sensitive adhesive layer being positioned between the facestock and the liner and being preferentially adherent to the facestock; said method comprising:

(A) cutting the pressure-sensitive adhesive construction with a first cutting step to form at least two shapes, the shapes being positioned in a side-by-side spaced relationship to each other and being of equal size and rectangular in shape, the long dimension of each shape being parallel to the long dimension of the next adjacent shape; the cut from the first cutting step being deep enough to penetrate the facestock; the cut from the first cutting step resulting in the formation of a matrix which comprises the waste facestock around the shapes;

(B) cutting the pressure-sensitive adhesive construction with a second cutting step to form at least one test sample, the second cutting step resulting in two parallel cuts through the pressure-sensitive adhesive construction, one of said parallel cuts being through one shape and the other parallel cut being through another shape adjacent to said one shape; the test sample comprising part of said one shape, part of said another shape, the matrix around said shape parts, and the adhesive and liner underlying the shape parts and matrix of the test sample;

(C) separating the matrix from the shape parts at a constant rate while measuring the force required to separate the matrix from the shape parts and measuring the displacement of the separating force; and (D) forming a plot of the force versus displacement measured in step (C), and determining the area under said plot, said area being a measure of the friction energy required to separate the matrix from the shape parts for said facestock, the selection of such pressure-sensitive construction, or a portion of said construction, being dependent on such friction energy measurement.

29. The method of claim 28 wherein the selection of said substrate comprises selection of the facestock of said substrate.

30. A method for selecting a substrate for use in a cutting operation, said method comprising:

predicting the die-cutting characteristics of a candidate substrate; and selecting the candidate substrate if its die-cutting characteristics are suitable for said cutting operation;

wherein said selection of the substrate includes the steps of:

(A) cutting the candidate substrate during a first cutting step to form at least two shapes in the candidate substrate, the shapes being positioned in spaced relationship to each other, a matrix being formed during said first cutting step, said matrix comprising the waste substrate around the shapes;

(B) cutting the candidate substrate with a second cutting step to form a test sample including a portion of the matrix;

(C) determining the frictional energy required to separate said portion of the matrix from said test sample; and (D) selecting the substrate for use in said cutting operation if the friction energy determined for said substrate is acceptable.

31. The method of claim 30 wherein said step of determining the frictional energy comprises separating said portion of the matrix from said test sample while measuring the force required to separate said portion of the matrix and measuring the displacement of the separating force.

32. The method of claim 30 wherein said second cutting step comprises cutting the test sample in such a manner that the test sample comprises part of a first shape, part of a second shape adjacent to said first shape, and the matrix around said first and second shapes.

* * * * *